(12) United States Patent
Ospina

(10) Patent No.: US 8,857,442 B1
(45) Date of Patent: Oct. 14, 2014

(54) HIGH LIP-LINE SMILE CORRECTIVE SURGICAL METHOD

(76) Inventor: Gloria A. Ospina, Coral Gables, FL (US)

(*) Notice: Subject to any disclaimer, the term of this patent is extended or adjusted under 35 U.S.C. 154(b) by 63 days.

(21) Appl. No.: 13/412,310

(22) Filed: Mar. 5, 2012

(51) Int. Cl.
*A61B 19/00* (2006.01)

(52) U.S. Cl.
USPC ............................................. 128/898

(58) Field of Classification Search
USPC ............................................. 128/898; 89/898
See application file for complete search history.

(56) References Cited

U.S. PATENT DOCUMENTS

| | | | |
|---|---|---|---|
| 5,093,179 A | 3/1992 | Scantlebury et al. | |
| 5,674,074 A | 10/1997 | Angelo, Jr. | |
| 6,019,764 A | 2/2000 | Bartee | |
| 6,149,434 A | 11/2000 | Gault | |
| 6,155,831 A | 12/2000 | McGuire | |
| 7,329,122 B1 | 2/2008 | Scott | |
| 7,748,979 B2 | 7/2010 | Nahlieli | |
| 2009/0081611 A1 | 3/2009 | Hines et al. | |
| 2010/0047733 A1 | 2/2010 | Nahlieli | |
| 2011/0032958 A1* | 2/2011 | Rizoiu et al. | 372/25 |
| 2011/0207075 A1 | 8/2011 | Altishuler et al. | |

OTHER PUBLICATIONS

Simon et al., Eliminating a Gummy Smile with Surgical Lip Repositioning, Clinical Science, vol. 23, No. 1, pp. 102-109, Spring 2007.*

Hwang et al., Surface Anatomy of the Lip Elevator Muscles for the Treatment of Gummy Smile Using Botulinum Toxin, Feb. 2008.*

* cited by examiner

*Primary Examiner* — Howie Matthews
(74) *Attorney, Agent, or Firm* — Albert Bordas, P.A.

(57) ABSTRACT

A high lip-line smile corrective surgical method. A first incision is made above a mucogingival junction to define a first edge. A second incision is made on attached gingiva above a gum line to define a second edge. Lift a section defined by the first and second incisions and remove the section with a micro scalp without affecting or contacting periosteum. Separate elevator muscles of the upper lip attached to the upper alveolar ridge with angulated gingevectomy scissors in reverse motion with release of tension so that the first and second edges meet. Seal the first and second edges with suture, individual stitches, or polypropylene; and cauterize the sealed the first and second edges.

9 Claims, 3 Drawing Sheets

HIGH LIP-LINE SMILE CORRECTIVE SURGICAL METHOD

BACKGROUND OF THE INVENTION

1. Field of the Invention

The present invention relates to cosmetic surgeries, and more particularly, to high lip-line smile corrective surgeries.

2. Description of the Related Art

Applicant believes that one of the closest references corresponds to U.S. Patent Application Publication No. 20110207075, published on Aug. 25, 2011 to Altishuler, et al. for Method and Apparatus for Regeneration of Oral Cavity Tissues. However, it differs from the present invention because Altishuler, et al. teach a method that comprises creating a predetermined pattern of treatment microzones in oral tissue affected by a condition, applying energy of predetermined characteristics to the soft tissue through a tip being limited by at least one dimensional feature of the oral tissue. The application of energy to the oral tissue after creating the predetermined pattern of treatment microzones in the oral soft tissue is terminated. A type of the energy and the characteristics of the predetermined pattern of treatment microzones are defined by the condition in the soft tissue. The condition in the oral tissue can be a gingival recession, gingivitis, periodontal disease, xerostomia, black triangle disease, and interdental/interimplant papilla deficiencies. The oral tissue can be oral soft tissue, such as oral mucosa soft tissue or a gingival soft tissue.

Applicant believes that another reference corresponds to U.S. Patent Application Publication No. 20090081611, published on Mar. 26, 2009 to Hines for Methods, Devices, Systems, Assemblies, and Kits for Tissue Retraction in an Oral Cavity. However, it differs from the present invention because Hines teaches a retraction device for retracting soft tissue from the dental surfaces in the oral cavity of a patient. The retraction device is comprised of a topology conformable structure, where the topology conformable structure is adaptable to be delivered to the oral cavity in a constrained shape. The device can then undergo a conformation change in the oral cavity, where the device transforms into its unconstrained shape. The unconstrained shape of the device creates a useable working field in the oral cavity. The useable working field can provide increased accessibility to and/or visibility within the oral cavity.

Applicant believes that another reference corresponds to U.S. Patent Application Publication No. 20100047733 and U.S. Pat. No. 7,748,979; published on Jul. 6, 2010 to Nahlieli for Device, System and Method for Dental Treatment. However, it differs from the present invention because Nahlieli teaches a device and system for use in a root canal treatment, the device having a probe member and a hand piece for holding the elongate probe member, the probe member having an elongate distal portion capable of being accommodated in a root canal, said probe member comprising: at least one treatment channel having a distal opening in said elongate distal portion, said at least one treatment channel being configured for enabling operation of a suitable root canal treatment tool via said distal opening; at least one illumination channel comprising a first light guide having a first proximal end configured for optical coupling to a light source system, and a second distal end in said distal portion for illuminating internal regions of the root canal during operation of said device; at least one light collection channel comprising a second light guide having a first proximal end configured for optical coupling to an imaging system, and a second distal end located in said distal portion for collecting and transmitting light reflected from internal regions of the root canal to said proximal end during operation of said device.

Applicant believes that another reference corresponds to U.S. Pat. No. 7,329,122 issued to Scott on Feb. 12, 2008 for Accelerated Orthodontic Apparatus and Method. However, it differs from the present invention because Scott teaches an apparatus and method for patients requiring repositioning of misaligned teeth who typically undergo orthodontic treatment to move the teeth into corrected positions. The orthodontic methods typically require lengthy procedures involving the application of light forces to the teeth to effect movement as accomplished by braces or other appliances. The apparatus and method includes the administration of a needle corticotomy to select regions that have been identified as absent any landmarks to avoid. The method is accomplished without the use of freeze-dried and bovine bone and without a mucoperiosteal flap procedure, resulting in low medical risk and providing a simplified and less time consuming procedure, and furthermore wherein the method effects a significant reduction in the time required to complete an orthodontic case while also significantly reducing the discomfort and recovery time for the patient.

Applicant believes that another reference corresponds to U.S. Pat. No. 6,155,831 issued to McGuire on Dec. 5, 2000 for Non-Surgically Retrievable Guided Tissue Regeneration Membrane. However, it differs from the present invention because McGuire teaches a dental appliance consisting of a biocompatible, non-absorbable retrievable membrane material that may be used as a separation and isolation barrier following periodontal surgery to promote tissue regeneration. The appliance is configured with a cord woven into the inferior aspect of the membrane and extends up from the apical border of the membrane through a loop in the superior border. The free end of the cord extends through the gingival sulcus and remains exposed while the membrane is in place. At the appropriate time for membrane removal, the sutures holding the membrane in place are released and the membrane removal cord is use to lift the membrane through the sulcus by gently pulling on the cord. The non-surgical removal of the membrane using this method reduces further surgical trauma to the patient and eliminates the risk that surgical removal of the membrane could damage the newly regenerated tissue.

Applicant believes that another reference corresponds to U.S. Pat. No. 6,149,434 issued to Gault on Nov. 21, 2000 for Method for Autogenous Transplantation of Human and Animal Teeth that Eliminates the Risk of Ankylosis and Root Resorption. However, it differs from the present invention because Gault teaches a method for transplanting human or animal teeth while eliminating the risk of ankylosis and root resorption. This method involves stimulating the periodontal ligament prior to transplanting the teeth by causing surgical trauma to the periodontal ligament by mobilization of the teeth (extraction and immediate replantation) and retaining them in a mobilized position to cause mechanical stimulation.

Applicant believes that another reference corresponds to U.S. Pat. No. 6,019,764 issued to Bartee on Feb. 1, 2000 for Method of Treating Alveolar Bone Defects. However, it differs from the present invention because Bartee teaches a method of repairing defects in alveolar bone underlying gingival tissue by placing a layer of flexible high-density polytetrafluoroethylene material over the alveolar bone defect between the bone and the gingival tissue surrounding the defect. The material has a smooth surface that will not incorporate cells and will not attach to fibrous adhesions. The gingival tissue is secured over the layer of material. The alveolar bone is allowed to heal under the layer of flexible high-density polytetrafluoroethylene material, and the layer of flexible high-density polytetrafluoroethlylene material is removed with substantially no trauma to the alveolar bone and gingival tissue.

Applicant believes that another reference corresponds to U.S. Pat. No. 5,674,074 issued to Angelo, Jr. on Oct. 7, 1997 for Periodontal Procedure. However, it differs from the present invention because Angelo, Jr. teaches a periodontal procedure for performing periodontal treatment including the steps of applying anesthetic to the area to be treated and making an incision on the facial side of the most posterior tooth and continuing the incision toward the most anterior tooth. The incision begins at the distal facial line angle of the most posterior tooth on the facial side of the arch and is made at about a forty-five degree angle to the plane of the tooth, forming an inverse bevel within the coronal portion of the pocket. A similar incision is made on the lingual side in the same manner. The incision is reentered to separate the facial, lingual, and papillary tissues from the underlying connective tissue so that the separated facial, lingual, papillary tissue may be removed, thereby removing the coronal portion of the tissue pocket and initially exposing root surfaces. The remaining tissue pocket is then removed. Soft tissue tags adjacent to the incised areas are also removed. Next, gross bacterial accretions on the root surface are removed followed by fine bacterial accretion removal. Post-treatment procedures to aid healing include light scaling of the teeth in the treated area followed by polishing of the teeth in the treated area with fluoride prophylaxis material and applying about a 30% trichloracetic acid to the facial, lingual, and proximal areas about seven days after treatment. The post-operative procedure is repeated seventeen days and thirty-one days after treatment.

Applicant believes that another reference corresponds to U.S. Pat. No. 5,093,179 issued to Scantlebury, et al. on Mar. 3, 1992 for Methods and Articles for Treating Periodontal Disease and Bone Defects. However, it differs from the present invention because Scantlebury, et al. teach a method for treatment of periodontal disease. The gingival tissue is separated from the tooth surface in an area where periodontal disease is present. A biocompatible, porous material such as expanded polytetrafluoroethylene capable of supporting ingrowth of gingival connective tissue and preventing apical migration of gingival epithelium is placed in a laminar relationship to a portion of the perimenter of the tooth surface. The gingival tissue is repositioned around the tooth and in contact with the porous material, with the porous material positioned between the gingival tissue and the tooth. Articles for the treatment of periodontal disease are also disclosed. One article comprises a first portion, which is capable of supporting ingrowth of gingival connective tissue and preventing apical migration of gingival epithelium and a second portion, which is impermeable to oral tissues and bacteria. Articles and methods for the treatment of bone defects are also disclosed. The articles have a first portion with a surface capable of supporting connective tissue ingrowth configured to contact the bone surrounding the defect and a second portion with a surface substantially impermeable to tissue ingrowth and bacteria invasion extending from the first portion to cover the defect.

Other patents describing the closest subject matter provide for a number of more or less complicated features that fail to solve the problem in an efficient and economical way. None of these patents suggest the novel features of the present invention.

SUMMARY OF THE INVENTION

The instant invention is a high lip-line smile corrective surgical method.

It is an object of this invention to provide such a method that is inexpensive to implement while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
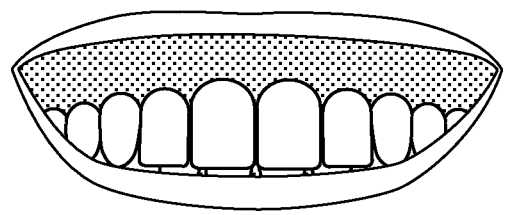
FIG. 1 is a representation of a patient's mouth illustrating a high lip-line smile, also defined as gummy smile, whereby more than desired alveolar ridge is exposed.

Referring now to the drawings, the present invention is a high lip-line smile corrective surgical method.

As seen in FIG. 1, a patient's mouth illustrates a high lip-line smile, also defined as gummy smile, whereby more than desired alveolar ridge is exposed.

The instant invention is a surgical method to restore alveolar ridge height by lowering the insertion of elevator muscles of the upper lip attached to the patient's upper alveolar ridge.

Figure 2:
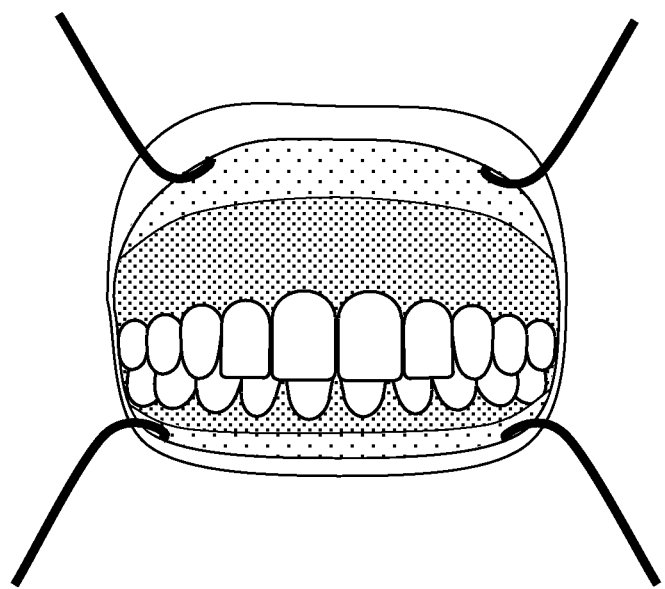
FIG. 2 is a first representation of select steps of the high lip-line smile corrective surgical method, object of the instant invention.

As seen in FIG. 2, performing the high lip-line smile corrective surgical method comprises: A) making a first incision above a mucogingival junction to define a first edge.

Step A) of the surgical method requires a laser device. The laser device uses water and air. In a preferred embodiment, a tapered tip, type T4 is used and the laser device is set at approximately 2.25 Watts. T4 defines a tapered tip and is 400 micrometers diameter. In a preferred embodiment, the laser device is in a soft-mode setting of approximately 20% water and 20% air. Alternate settings may be of approximately 30% water and 20% air.

With approximately a 2 mm distance above the attached gingiva, the first incision is made by tracing over markings on a patient's upper alveolar ridge, whereby the markings are made by the surgeon or qualified medical personnel while the patient presents a biggest smile to expose the upper alveolar ridge. The first incision is made at approximately a 45-degree angle from the upper alveolar ridge above the markings on the patient's upper alveolar ridge and is made closest to the maxillary bone without touching periosteum of the upper alveolar ridge.

The high lip-line smile corrective surgical method further comprises: B) making a second incision on attached gingiva above a gum line to define a second edge.

Step B) of the surgical method requires the laser device be in the soft-mode setting of approximately 20% water and 20% air. In a preferred embodiment, the laser device is set at approximately 2.25 watts and the second incision is made with a Z3 tip. The Z3 tip is a chisel shape and has dimensions of 300 micrometers per 1200 micrometers. The second incision can also made with a G6 tip that is a cylindrical tip of 600 micrometers.

The second incision is made approximately 4-5 mm above the gum line of the upper alveolar ridge all the way to the other side of the mouth. The second incision will be made approximately at a 90-degree angle from the upper alveolar ridge angle against the bone with out touching the periosteum of the upper alveolar ridge.

The first and second incisions are made with the laser device that utilizes water to perform cutting procedures, whereby laser energy is passed through a mist of water spray. Water-particles shoot forward and hit the target tissue as the laser energizes them. The water-particles hit the cells and evaporate the cells water contents and the cells collapse.

The high lip-line smile corrective surgical method further comprises: C) lifting section defined by said first and second incisions and removing said section with a micro scalp without affecting or contacting the periosteum.

Step C) of the surgical method includes using a micro-scalp or flexible blade, whereby the micro-scalp or flexible blade is bent to approximately a 60-degree angle using a hemostat or tissue forcep. A farthest end of said section is grabbed and all connective tissue between said first and second incisions is removed, preserving membrane that covers said periosteum. The micro-scalp or flexible blade is a bendable micro-blade having a full radius.

If required, the surgical method further includes locating a most protuberant bone section or exostosis and exposing it by removing the periosteum. With an ultrasonic device having a tip of approximately a 45-degree angle, all of the most protuberant bone section or exostosis is removed in layers (osteoplasty) up to the patient's maxilla. The purpose of removing the most protuberant bone section or exostosis is to force tissue lower and to lower the insertion of elevator muscles of the upper lip attached to the patient's upper alveolar ridge to reduce the patient's upper alveolar ridge. It is noted that for minor cases, the osteoplasty procedure may be performed after Step C) defined above. However, if defined as beyond a minor case or at the advice of the surgeon or qualified medical personnel, the osteoplasty procedure may performed at a predetermined time period before the present high lip-line smile corrective surgical method. Such a predetermined time period may be several weeks to allow for proper healing.

The high lip-line smile corrective surgical method further comprises: D) separating elevator muscles of the upper lip attached to the patient's upper alveolar ridge with angulated gingevectomy scissors in reverse motion with release of tension so that said first and second edges meet. The reverse motion is best performed with the tip of the gingivectomy scissors to carefully cut surrounding fibers as required.

Figure 3:
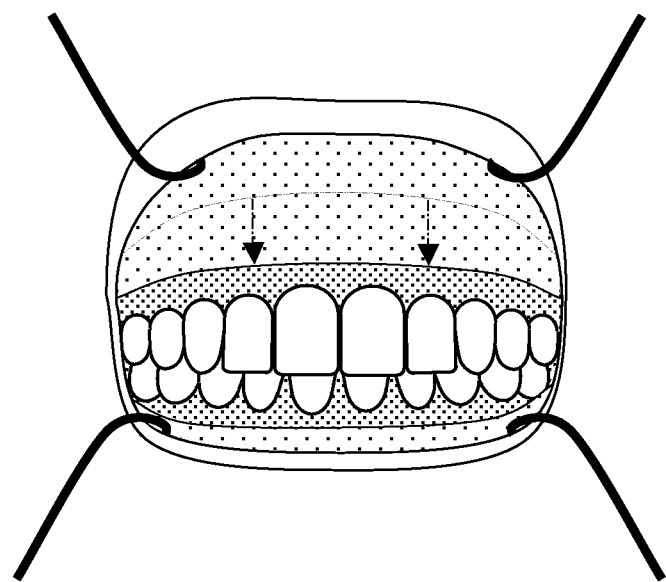
FIG. 3 is a second representation of select steps of the high lip-line smile corrective surgical method.

Step D) of the surgical method, and specifically reverse motion, includes dissecting tissue above said first incision using serrated gingivectomy scissors, to elevator muscles of the upper lip. Thus, enabling to pull the first edge to reach the second edge as seen in FIG. 3.

The high lip-line smile corrective surgical method further comprises: E) sealing said first and second edges with suture, individual stitches, or polypropylene.

Step E) of the surgical method includes ensuring that the tissue above the first edge is loose and falls freely over the second edge so that suture is placed individually at a papilla level of each tooth.

The high lip-line smile corrective surgical method further comprises: F) cauterizing said sealed first and second edges.

Step F) of the surgical method includes cauterizing the sealed first and second edges with the laser device. In a preferred embodiment, the laser device is set at approximately 1.75 watts, however without water and 20% air. Cauterizing promote healing of the sealed first and second edges.

In a preferred embodiment, the laser device is one manufactured by BioLase Technology, Inc. under the trademark ("WATERLASE"), defined as a lasers and cutting or ablating device used in combination with fluids for medical use.

Additionally, the surgical method includes administering predetermined amounts of botulinum toxin neurotoxic protein to the patient. Administration is best performed by injection, whereby the botulinum toxin neurotoxic protein is injected at the obicularis oris just below the nostrils. Additionally, botulinum toxin neurotoxic protein may also be injected deep into muscle between each zygomatic bone and lateral sides of the nose. In a preferred embodiment, the predetermined amounts of botulinum toxin neurotoxic protein are approximately 5 units but will depend on each respective patient and their needs.

Figure 4:
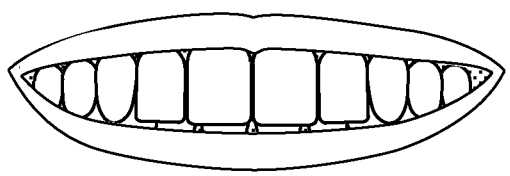
FIG. 4 is a representation of the patient's mouth after the high lip-line smile corrective surgical method, whereby desired alveolar ridge is exposed.

As seen in FIG. 4, the patient's mouth, after the high lip-line smile corrective surgical method, has a desired alveolar ridge exposed as compared to FIG. 1.

Therefore, the present invention is a high lip-line smile corrective surgical method, comprising the steps of:
A) making a first incision above a mucogingival junction to define a first edge;
B) making a second incision on attached gingiva above a gum line to define a second edge;
C) lifting section defined by said first and second incisions and removing said section with a micro scalp without affecting or contacting periosteum;
D) separating elevator muscles of upper lip attached to upper alveolar ridge with angulated gingevectomy scissors in reverse motion with release of tension so that said first and second edges meet;
E) sealing said first and second edges with suture, individual stitches, or polypropylene; and
F) cauterizing said sealed first and second edges.

Figure 5:
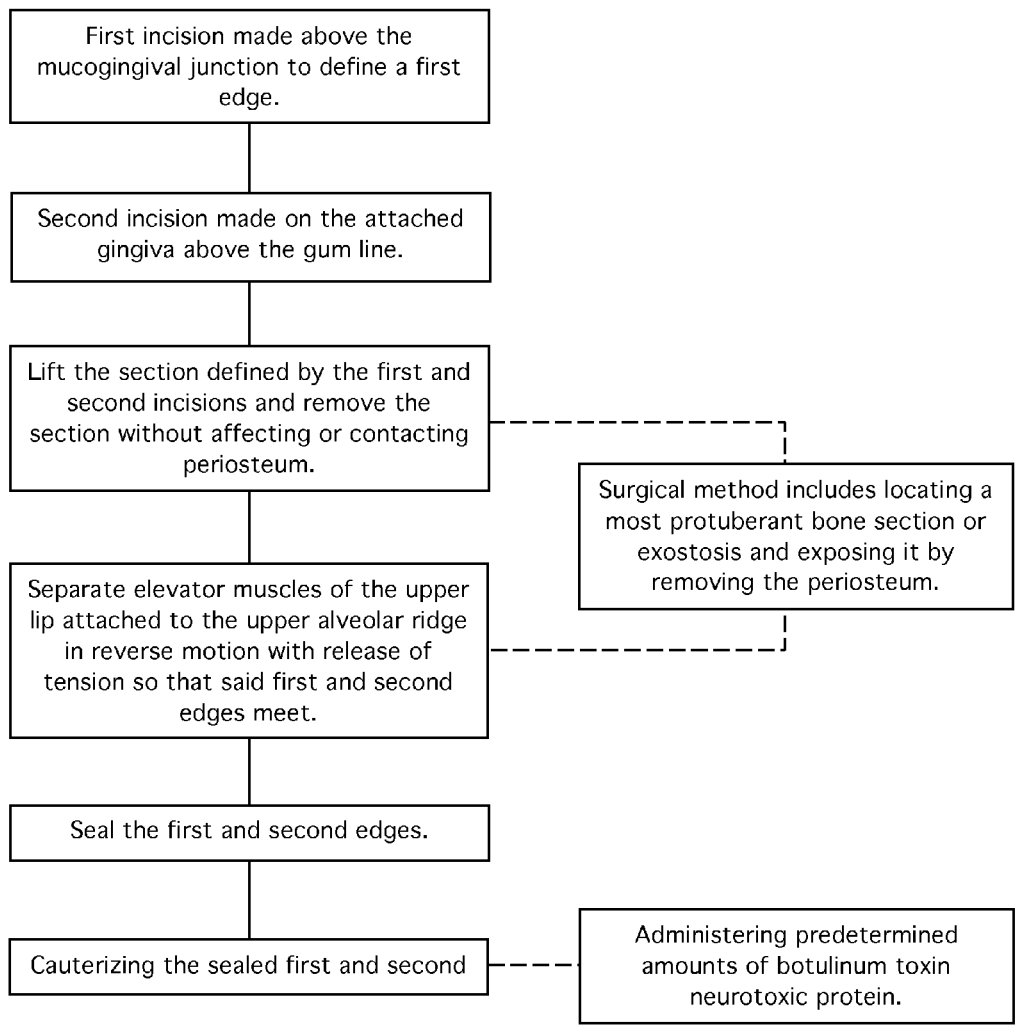
FIG. 5 is a flowchart describing select steps of the high lip-line smile corrective surgical method.

As seen in FIG. 5, a flowchart illustrates select steps of the high lip-line smile corrective surgical method.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A high lip-line smile corrective surgical method, comprising the steps of:
A) making a first incision with a laser device above a mucogingival junction to define a first edge, said first incision is made by tracing over markings on an upper alveolar ridge at approximately a 45-degree angle from said upper alveolar ridge angle, and approximately at a 2 mm distance above attached gingiva, said first incision is further made at a maxillary bone without touching periosteum of said upper alveolar ridge;
B) making a second incision with said laser device on said attached gingiva to define a second edge, said second incision is made approximately at a 90-degree angle from said upper alveolar ridge angle against bone without touching said periosteum of said upper alveolar ridge, and approximately at 4-5 mm above a gum line of said upper alveolar ridge, said first edge and said second edge together form a section, said laser device utilizes water to perform cutting procedures, whereby laser energy is passed through a mist of water spray, water-particles shoot forward and hit target tissue as a laser energizes them, said water-particles hit cells and evaporate cells water contents and said cells collapse, for said second incision said laser device is in a soft-mode setting of approximately 20% water and 20% air;

C) lifting said section and removing with a micro scalp or a flexible blade without affecting or contacting said periosteum, whereby said section is grabbed and connective tissue between said first and second incisions is removed while membrane is preserved that covers said periosteum;

D) separating elevator muscles of upper lip attached to said upper alveolar ridge with angulated gingevectomy scissors in reverse motion with release of tension so that said first and second edges meet;

E) sealing said first and second edges with suture, individual stitches, or polypropylene, whereby said first edge is loose and falls freely over the second edge so that said suture, individual stitches, or polypropylene is placed individually at a papilla level of each tooth; and F) cauterizing said sealed first and second edges with said laser device to promote healing of said sealed first and second edges.

2. The high lip-line smile corrective surgical method set forth in claim 1, further comprising the steps of locating a most protuberant bone section or exostosis and exposing it by removing said periosteum, said most protuberant bone section or exostosis is removed in layers up to a maxilla, whereby removing said most protuberant bone section or exostosis allows lowering of said elevator muscles of said upper lip attached to said upper alveolar ridge to reduce said upper alveolar ridge.

3. The high lip-line smile corrective surgical method set forth in claim 1, further characterized in that said reverse motion is performed with said gingivectomy scissors tip to cut surrounding fibers, whereby said reverse motion includes dissecting tissue above said first incision to said elevator muscles of said upper lip, so that said first edge reaches said second edge.

4. The high lip-line smile corrective surgical method set forth in claim 1, further comprising the steps of administering predetermined amounts of botulinum toxin neurotoxic protein, said administering is by injection at obicularis oris just below nostrils and into muscle between each zygomatic bone and lateral sides of nose.

5. A high lip-line smile corrective surgical method, comprising the steps of:
A) making a first incision with a laser device above a mucogingival junction to define a first edge, said first incision is made by tracing over markings on an upper alveolar ridge at approximately a 45-degree angle from said upper alveolar ridge, and approximately at a 2 mm distance above attached gingiva, said first incision is further made at a maxillary bone without touching periosteum of said upper alveolar ridge;

B) making a second incision with said laser device on said attached gingiva to define a second edge, said second incision is made approximately at a 90-degree angle from said upper alveolar ridge angle against bone without touching said periosteum of said upper alveolar ridge, and approximately at 4-5 mm above a gum line of said upper alveolar ridge, said first edge and said second edge together form a section, said laser device utilizes water to perform cutting procedures, whereby laser energy is passed through a mist of water spray, water-particles shoot forward and hit target tissue as a laser energizes them, said water-particles hit cells and evaporate cells water contents and said cells collapse, for said second incision said laser device is in a soft-mode setting of approximately 20% water and 20% air;

C) lifting said section and removing with a micro scalp or a flexible blade without affecting or contacting said periosteum, whereby said section is grabbed and connective tissue between said first and second incisions is removed while membrane is preserved that covers said periosteum;

D) separating elevator muscles of upper lip attached to said upper alveolar ridge with angulated gingevectomy scissors in reverse motion with release of tension so that said first and second edges meet, said reverse motion is performed with said gingivectomy scissors tip to cut surrounding fibers, whereby said reverse motion includes dissecting tissue above said first incision to said elevator muscles of said upper lip, so that said first edge reaches said second edge;

E) sealing said first and second edges with suture, individual stitches, or polypropylene, whereby said first edge is loose and falls freely over the second edge so that said suture, individual stitches, or polypropylene is placed individually at a papilla level of each tooth;

F) cauterizing said sealed first and second edges with said laser device to promote healing of said sealed first and second edges; and G) administering predetermined amounts of botulinum toxin neurotoxic protein, said administering is by injection at obicularis oris just below nostrils and into muscle between each zygomatic bone and lateral sides of nose.

6. The high lip-line smile corrective surgical method set forth in claim 5, further comprising the steps of locating a most protuberant bone section or exostosis and exposing it by removing said periosteum, said most protuberant bone section or exostosis is removed in layers up to a maxilla, whereby removing said most protuberant bone section or exostosis allows lowering of elevator muscles of upper lip attached to said upper alveolar ridge to reduce said upper alveolar ridge.

7. A high lip-line smile corrective surgical method, comprising the steps of:
A) making a first incision with a laser device above a mucogingival junction to define a first edge, said first incision is made by tracing over markings on an upper alveolar ridge at approximately a 45-degree angle from said upper alveolar ridge, and approximately at a 2 mm distance above attached gingiva, said first incision is further made at a maxillary bone without touching periosteum of said upper alveolar ridge;

B) making a second incision with said laser device on said attached gingiva, below said first incision, to define a second edge, said second incision is made approximately at a 90-degree angle from said upper alveolar ridge angle against bone without touching said periosteum of said upper alveolar ridge, and approximately at 4-5 mm above a gum line of said upper alveolar ridge, said first edge and said second edge together form a section, said laser device utilizes water to perform cutting procedures, whereby laser energy is passed through a mist of water spray, water-particles shoot forward and hit target tissue as a laser energizes them, said water-particles hit cells and evaporate cells water contents and said cells collapse, for said second incision said laser device is in a soft-mode setting of approximately 20% water and 20% air;

C) lifting said section and removing with a micro scalp or a flexible blade without affecting or contacting said periosteum, whereby said section is grabbed and connective tissue between said first and second incisions is removed while membrane is preserved that covers said periosteum;

D) locating a most protuberant bone section or exostosis and exposing it by removing said periosteum, said most protuberant bone section or exostosis is removed in layers up to a maxilla, whereby removing said most protuberant bone section or exostosis allows lowering of elevator muscles of upper lip attached to said upper alveolar ridge to reduce said upper alveolar ridge;

E) separating elevator muscles of upper lip attached to said upper alveolar ridge with angulated gingevectomy scissors in reverse motion with release of tension so that said first and second edges meet;

F) sealing said first and second edges with suture, individual stitches, or polypropylene, whereby said first edge is loose and falls freely over the second edge so that said suture, individual stitches, or polypropylene is placed individually at a papilla level of each tooth; and G) cauterizing said sealed first and second edges with said laser device to promote healing of said sealed first and second edges.

8. The high lip-line smile corrective surgical method set forth in claim 7, further characterized in that said reverse motion is performed with said gingivectomy scissors tip to cut surrounding fibers, whereby said reverse motion includes dissecting tissue above said first incision to said elevator muscles of said upper lip, so that said first edge reaches said second edge.

9. The high lip-line smile corrective surgical method set forth in claim 8, further comprising the steps of administering predetermined amounts of botulinum toxin neurotoxic protein, said administering is by injection at obicularis oris just below nostrils and into muscle between each zygomatic bone and lateral sides of nose.

* * * * *